United States Patent [19]

Miyazawa et al.

[11] 4,351,830

[45] Sep. 28, 1982

[54] POLYMERIC COMPOUND, MF-300, WITH PROTECTIVE ACTIVITY AGAINST BACTERIAL INFECTIONS AND ITS PREPARATION

[75] Inventors: Takeo Miyazawa; Takahiro Ishii, both of Tokyo; Yuzo Kazuno, Hachioji; Eiichi Akita, Yokohama; Yujiro Yamada, Yokohama; Taro Niida, Yokohama, all of Japan

[73] Assignee: Meiji Seika Kaisha, Ltd., Tokyo, Japan

[21] Appl. No.: 269,609

[22] Filed: Jun. 2, 1981

[30] Foreign Application Priority Data

Jun. 17, 1980 [JP] Japan .................................. 55/80847

[51] Int. Cl.³ ...................... A61K 31/73; C07H 15/22
[52] U.S. Cl. .................................... 424/180; 536/16.8
[58] Field of Search ...................... 536/17 R; 424/180

[56] References Cited

U.S. PATENT DOCUMENTS

| | | | |
|---|---|---|---|
| 4,125,706 | 11/1978 | Umezawa et al. | 536/17 R |
| 4,169,890 | 10/1979 | Miyazawa et al. | 536/17 R |
| 4,170,641 | 10/1979 | Akita et al. | 536/17 R |

*Primary Examiner*—Johnnie R. Brown
*Attorney, Agent, or Firm*—Larson and Taylor

[57] ABSTRACT

A new polymeric compound, MF-300, is provided, which possesses a specific protective activity against bacterial infections caused particularly by *Pseudomonas aeruginosa*. The compound is derived from the reaction of ribostamycin with crotonoyl chloride followed by concentration of the reaction product and by subsequent recovery therefrom of a fraction having a range of molecular weights of 10,000~100,000 when measured by ultrafiltration method.

4 Claims, 2 Drawing Figures

POLYMERIC COMPOUND, MF-300, WITH PROTECTIVE ACTIVITY AGAINST BACTERIAL INFECTIONS AND ITS PREPARATION

FIELD OF THE INVENTION

This invention relates to a new polymeric compound designated as MF-300 which is derived from the reaction of ribostamycin with crotonoyl chloride in an aqueous organic solvent in the presence of a base followed by fractionating the reaction product according to the difference in molecular weight. This invention further relates to a process for the preparation of the compound MF-300 and to a water-soluble pharmaceutical composition containing the same as active ingredient due to a protective activity thereof against bacterial infections.

BACKGROUND OF THE INVENTION

It is known that some macromolecular substances have the effect of potentiating immunological response in vivo. Thus, it is well-known that a water-insoluble residue recovered from the products obtained by autolysis or protease-treatment of yeast cell walls takes part in the immunological defense mechanism of a living animal and exhibits a protective action against bacterial infections. An example of such water-insoluble residue is a substance designated as "Zymosan" [see Nagy et al., Archivo Italiano di Patologia e Clinica der Tumori, XIV, Fasc. 3~4, pages 29~35 (1971); F. W. Fitzpatrick, F. I. Dicarlo, Ann. New York Acad. Sci., 118 (4), pages 233~262 (1964)]. In the 25th General Meeting of the Japan Chemotherapy Society (see Summary Report, page 157, issued on June 11, 1976), it is proposed that Zymosan is used as a standard drug to evaluate the activity of Picibanil to protect against the infection by some bacteria of genus Staphylococus.

Reference is further made to Japanese Patent KOKAI (Preliminary Publication) No. 70809/76 and No. 29215/76, which disclose immunopotentiating effect of a material constituting yeast cell wall hydrolyzate. Japanese Patent KOKAI No. 27101/80 discloses prophylactic and therapeutic effects on infectious diseases of KS-2-A substance which is produced by culturing a mycelium.

In recent years, it has been reported that N-acetylmuramyl-L-alanyl-D-isoglutamine (Japanese Patent KOKAI No. 41211/77) and N-acetylmuramyl-L-alanyl-D-glutamine (Japanese Patent KOKAI No. 44223/77) possess a high adjuvant effect as water-soluble, low-molecular weight immunopotentiator. It has also been found that orthobenzoic acid oxide exhibits a protective activity against bacterial infections (Chem. Pharm. Bull., 2143 (1977), Japanese Patent KOKAI No. 41041/76 and Japanese Patent KOKAI No. 12141/77) and that a certain aziridine derivative provides an increased degree of resistance to bacterial infections (Japanese Patent KOKAI No. 111563/77).

As described above, there are a variety of compounds derived through a synthetic route, which have already been proposed as protective agent against bacterial infections, but all these compounds are entirely different in chemical nature from the new compound according to this invention. Thus, the orthobenzoic acid oxide is of skeleton of an aromatic ring (Japanese Patent KOKAI No. 41041/76 and No. 12141/77) and the aziridine derivative is of skeleton of three-membered ring (Japanese Patent KOKAI No. 111563/77). Examples of low-molecular weight immunopotentiator already proposed are 4-imino-1,3-diazobicyclo[3,1,0]hexan-2-one (Japanese Patent KOKAI No. 10290/77), N-2-(6-hydroxybenzothiazolyl)-N'-substituted or unsubstituted phenylurea (Japanese Patent KOKAI No. 59860/76) and pyrrolidine derivatives (Japanese Patent KOKAI No. 98299/76). Examples of higher-molecular weight immunopotentiator are fatty acid esters of fructose and sucrose (Japanese Patent KOKAI No. 29291/76), fatty acid esters of glucose and trehalose (Japanese Patent KOKAI No. 29292/76), 6,6'-dimycolate of trehalose (Cancer Imm. Immunother, 1, 227 (1976)) and 6-mycoloyl-N-acetylmuramyl-L-alanyl-D-isoglutamine (IUPAC A.P. 6C2-14 (1977)).

We have now prepared a new polymeric compound derived from the reaction of ribostamycin with crotonoyl chloride and found that it has no antibacterial activity in vitro and is not metabolized in vivo into a substance having an antibacterial activity, but unexpectedly it exhibits a protective activity against bacterial infection in vivo.

SUMMARY OF THE INVENTION

According to the first aspect of this invention, therefore, there is provided a new polymeric compound, MF-300, which is obtained by reacting ribostamycin with crotonoyl chloride, concentrating and purifying the reaction product and recovering the compound therefrom as a fraction having a range of molecular weights of 10,000~100,000 when measured by ultrafiltration method and which has the following properties:

(1) Elemental analysis: C, 48.52±2.16%; H, 7.24±0.24%; N, 8.04±1.02%; Cl, 5.05±0.3%.

(2) Molecular weight: 10,000~100,000 (when measured by ultrafiltration); 15,000~70,000 (when measured by ultracentrifuge).

(3) Appearance: Pale yellow, amorphous powder.

(4) Decomposition point: 170°~200° C.

(5) Specific rotation: $[\alpha]_D^{25} +40.4° \pm 7.3°$ (c 1.0, $H_2O$).

(6) Infrared absorption: 3400, 2940, 1660, 1630, 1550 $cm^{-1}$.

(7) Ultraviolet absorption: No specific maximum absorption.

(8) NMR spectrum: 1.0~1.5, 1.8~2.1, 3.2~4.2, 5.2~5.4, 5.6~6.3, 6.5~7.2 ppm.

(9) Nature of aqueous solution: pH 4~6 (1% aqueous solution).

(10) Solubility: Soluble in water and methanol. Insoluble in ethanol, chloroform, acetone and petroleum ether.

(11) Color reaction: Positive to anthrone and Molisch reactions. Weakly positive to ninhydrin and biuret reactions. Negative to Tollens reaction.

Thus, the compound according to this invention is basically differentiated in chemical nature from any of the known immunopotentiators above-referred to and belongs to a new class of substances as protective agent against bacterial infections.

DETAILED DESCRIPTION OF THE INVENTION

The new polymeric compound, MF-300, may be prepared according to this invention by reacting ribostamycin with crotonoyl chloride in an aqueous organic solvent in the presence of a base, concentrating the reaction product and recovering therefrom a fraction having a range of molecular weights of 10,000~100,000 when measured by ultrafiltration method.

In a typical embodiment of the process according to this invention, ribostamycin in an aqueous organic solvent is rapidly reacted with 1 to 36 moles per mole of ribostamycin of crotonoyl chloride at 0°~150° C. in the presence of a base. The resulting reaction mixture is concentrated to dryness, dissolved in water and washed with ethyl acetate or chloroform to remove any excess of the reagents and solvent used. The aqueous layer is then concentrated to dryness, yielding MF-300 in the form of hydrochloride. The crude product thus obtained is again dissolved in water and subjected to ultrafiltration to recover a fraction of the desired molecular weight range.

Examples of aqueous organic solvents may include aqueous dimethylformamide, methanol, ethanol, acetone, dioxane, tetrahydrofuran, diglyme, pyridine and acetonitrile. The base acts as acid-binder and may be an organic base, for example, a tri-lower alkylamine such as trimethylamine and triethylamine, or an inorganic base, for example, an alkali metal carbonate such as sodium carbonate or an alkali metal hydrogen carbonate such as sodium hydrogen carbonate. A typical ultrafiltration apparatus is one using "Diaflow membrane" (a molecular sieve membrane made by Amicon Far East Limited, U.S.A.).

The new compound MF-300 according to this invention does not pass through the "Diaflow membrane PM 10" having the pore diameter corresponding to the size of substances of the molecular weight of 10,000, but passes through the "Diaflow membrane XM 100A" having the pore diameter corresponding to the size of substances of the molecular weight of 100,000. Thus, the estimated molecular weight of the new compound is 10,000~100,000.

Further, it has been observed that the compound MF-300, when passed through the "Diaflow membrane PM-30" having the pore diameter corresponding to the size of substances of the molecular weight of 30,000 or the "Diaflow membrane XM-50" having the pore diameter corresponding to the size of substances of the molecular weight of 50,000, distributes its activities between the passed and remaining fractions, apart from the difference in degree of activities. Therefore, it is believed that the compound MF-300 is a polymer having a molecular weight distribution ranging 10,000~100,000 and comprising ribostamycin moiety and crotonic acid moiety and/or butyryl chain as constituents.

In order to study on the chemical structure of the compound MF-300, we carried out an alkaline hydrolysis of the compound. Since the NMR spectrum of the compound MF-300 indicated the presence of crotonoyl group in the molecule, which may suggest the possibility of the addition of an amino group of ribostamycin to the double bond of crotonyl group during the alkaline hydrolysis, the hydrolysis was preceded by the addition of hydrazine hydrate which is a more nucleophilic reagent whereby to saturate the double bond of crotonoyl group. Six kinds of compounds in the hydrolysate were obtained, of which main four (A)~(D) were confirmed to have the following structures:

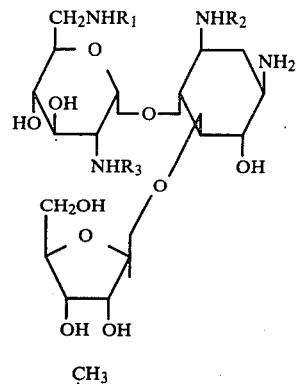

(A): $R_1 = -\overset{CH_3}{\underset{|}{CH}}-CH_2COOH$, $R_2 = R_3 = H$ (B): $R_2 = -\overset{CH_3}{\underset{|}{CH}}-CH_2COOH$, $R_1 = R_3 = H$ (C): $R_3 = -\overset{CH_3}{\underset{|}{CH}}-CH_2COOH$, $R_1 = R_2 = H$ (D): $R_1 = R_2 = R_3 = H$ (ribostamycin)

The determination of the structure was mainly based on the analyses of C-13 and H-1 nuclear magnetic resonance spectra and mass spectrum.

Elemental analysis, specific rotation and melting point of each of the hydrolysates (A), (B) and (C) are as follows:

(A) Elemental analysis (for $C_{21}H_{40}N_4O_{12}.4/5\ H_2O$): Found: C, 45.53; H, 7.61; N, 9.86%. Calculated: C, 45.45; H, 7.56; N, 10.10%. $[\alpha]_D^{25} +33.0°$ (c 1.0, $H_2O$), m.p. 134°~137° C.

(B) Elemental analysis (for $C_{21}H_{40}N_4O_{12}.H_2O$): Found: C, 45.44; H, 7.58; N, 10.01%. Calculated: C, 45.15; H, 7.58; N, 10.03%. $[\alpha]_D^{25} +45.3°$ (c 1.0, $H_2O$), m.p. 159°~164° C.

(C) Elemental analysis (for $C_{21}H_{40}N_4O_{12}.3/2\ H_2O$): Found: C, 44.61; H, 7.27; N, 9.83%. Calculated: C, 44.44; H, 7.64; N, 9.87%. $[\alpha]_D^{25} +48.1°$ (c 1.0, $H_2O$), m.p. 190°~194° C.

On the basis of the structures of the compounds in the hydrolysate above-mentioned, the monomer from which the compound MF-300 was derived may be estimated to have the structure:

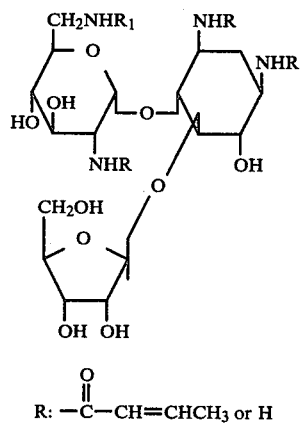

R: $-\overset{O}{\underset{\|}{C}}-CH=CHCH_3$ or H

Therefore, it is presumed that the compound MF-300 is a polymer derived from crotonoyl ribostamycin as monomer wherein a free amino group of a crotonoyl ribostamycin molecule was added to a crotonoyl group of the adjacent molecule of the monomer. The presence of the compounds (A), (B) and (C) in the hydrolysate clearly shows that the position at which two monomeric molecules were linked are not fixed. Thus, the estimated structure of the compound MF-300 hydrochloride is as follows:

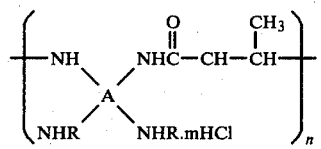

In the same manner as that used in the process according to this invention, it is possible to obtain similar active substances from other amino sugars such as neamine, 2-deoxystreptamine and the like.

The protective activity of the compound MF-300 against *Pseudomonas aeruginosa* in vivo was evaluated in the following Experiments A and B.

EXPERIMENT A

Test animals

JCL/ICR mice (about 4 weeks old; average body weight 21.4 g) were used in groups each consisting of 7 males.

Test compound

MF-300. Zymosan A as control, produced by Sigma Co., Lot 106 C-0352.

Test strains

*Pseudomonas aeruginosa* E2.

Bacterial cell suspensions

The original bacterial cell suspension was prepared by smearing the test strain on a plate of heart infusion agar (Difco), cultivating it at 37° C. for 20 hours, isolating the bacterial cells from the plate and suspending the cells in sterilized physiological saline solution to give a cell suspension having a value of optical density corresponding to the graduation of 200 on Klett-Summerson photoelectric colorimeter. The diluted cell suspensions used for the inoculation were prepared by diluting the original cell suspension with the same saline solution as used above at different rates of dilution required and mixing each of the diluted suspensions with 5% aqueous mucin solution in equal proportions. The volume inoculated of the resulting suspensions each was 0.5 ml/mouse.

Dosage of compound administered 100, 25, 6.25 and 1.56 μg/mouse for MF 300; 4, 1 and 0.25 mg/mouse for Zymosan A. Each solution of the compounds was prepared with the addition of a required amount of a sterilized distilled water.

Test procedure

The test compound specified above was administered subcutaneously at the dosages indicated to the femoral region of mice. Five days after the administration, the bacterial cell suspension prepared above was inoculated intraperitoneally to the mice, after which the number of the mice survived was counted during 5 days.

Test results (i) The number of mice survived for 5 days after the inoculation is shown in Table 1.

(ii) $LD_{50}$ inoculum size of the bacterial cell at each dosage of compound administered is shown in Table 2.

(iii) $ED_{50}$ of the test compound for different inoculum sizes of the bacteria is shown in Table 3.

These results show the protective activity of MF-300 to be extremely superior to that of Zymosan A. Thus, in comparison with the untreated control, $LD_{50}$ value of the bacterial cell increased 230 times at a dosage of 100 μg/mouse of MF-300, whereas $LD_{50}$ value of the bacterial cell only increased 23 times at a dosage of 4 mg/mouse of Zymosan A and 3.8 times at a dosage of 1 mg/mouse of Zymosan A. Further, the comparison in $ED_{50}$ values between MF-300 and Zymosan A shows that at the inoculum size of 7.2 $LD_{50}$, $ED_{50}$ value of MF-300 was less than 1.56 μg/mouse, whereas $ED_{50}$ value of Zymosan A was 1.2 mg/mouse and at the inoculum size of 72 $LD_{50}$, $ED_{50}$ value of MF-300 was 33 μg/mouse, whereas $ED_{50}$ value of Zymosan A was higher than 4 mg/mouse.

TABLE 1

| Number of bacterial cells inoculated | MF - 300 | | | | Zymosan A | | | Control (untreated) |
|---|---|---|---|---|---|---|---|---|
| | \multicolumn{7}{c}{Dosage} | | |
| | 100μg | 25μg | 6.25μg | 1.56μg | 4mg | 1mg | 0.25mg | 0 |
| 7.2 × 10⁵ | 1/7 | 0/7 | | | 1/7 | | | |
| 7.2 × 10⁴ | 6/7 | 2/7 | 1/7 | 3/7 | 2/7 | 1/7 | 0/7 | 0/7 |
| 7.2 × 10³ | 6/7 | 7/7 | 7/7 | 4/7 | 7/7 | 3/7 | 0/7 | 1/7 |
| 7.2 × 10² | | | 7/7 | 6/7 | | 7/7 | 5/7 | 4/7 |
| 7.2 × 10¹ | | | | | | | | 7/7 |

Number of mice survived/Number of mice tested

TABLE 2

| Compound | Dosages | $LD_{50}$ (cells/mouse) of bacterial cell | Ratio to the control |
|---|---|---|---|
| MF-300 | 100μg | 2.3 × 10⁵ | 230.0 |
| | 25μg | 4.0 × 10⁴ | 40.0 |
| | 6.25μg | 2.3 × 10⁴* | 23.0 |
| | 1.56μg | 1.1 × 10⁴* | 11.0 |
| Zymosan A | 4mg | 2.3 × 10⁴ | 23.0 |
| | 1mg | 3.8 × 10³ | 3.8 |
| | 0.25mg | 2.3 × 10³* | 2.3 |
| Control (untreated) | 0 | 1.0 × 10³ | 1.0 |

*Estimated value

TABLE 3

| Bacteria Inoculum size | Compound | $ED_{50}$ |
|---|---|---|
| 72 $LD_{50}$ | MF-300 | 33.0 (11.7–92.4)μg/mouse |
| | Zymosan A | >4mg/mouse |
| 7.2 $LD_{50}$ | MF-300 | <1.56μg/mouse |
| | Zymosan A | 1.2 (0.44–3.24)mg/mouse |

EXPERIMENT B

Test animals

JCL/ICR mice (about 4 weeks old; average body weight 20.0 g) were used in groups each consisting of 6 males.

Test compound: Same as those used in Experiment A.

Test strain: *Pseudomonas aeruginosa* IFO-3455

Bacterial cell suspensions: Prepared by the same method as in Experiment A.

Dosage of compound administered: 100 and 10 μg/mouse for MF-300; 1 mg/mouse for Zymosan A. Each solution of the compounds was prepared by the addition of a required amount of a sterilized distilled water.

Test procedure: Same as that used in Experiment A.

Test results: The number of mice survived after the lapse of 5 days for observation is shown in Table 4.

TABLE 4

| Number of bacterial cells inoculated | Compound | | | |
|---|---|---|---|---|
| | MF - 300 | | Zymosan A | Control (untreated) |
| | Dosage | | | |
| | 100μg | 10μg | 1mg | 0 |
| 5.8 × 10⁵ | 2/6 | 0/6 | | |
| 5.8 × 10⁴ | 6/6 | 6/6 | 1/6 | 0/6 |
| 5.8 × 10³ | 6/6 | 4/6 | 4/6 | 1/6 |
| 5.8 × 10² | | | 6/6 | 5/6 |
| 5.8 × 10¹ | | | | 5/6 |

Number of mice survived/Number of mice tested

The results above show that the protective activity of MF-300 was much higher at a dosage of 100 μg/mouse than, and appreciably superior even at a dosage of 10 μg/mouse to, that of Zymosan A at a dosage of 1 mg/mouse.

Further, it has been observed that the toxicity of the compound MF-300 is low to such an extent that a subcutaneous injection thereof into mice at a dosage of 500 mg/kg causes no notable change in the conditions of the test mice with all the mice surviving.

Taking the fact into consideration that the compound MF-300 does not directly attack and destroy pathogenic bacteria, the protective activity of this compound against the bacterial infections will be understood well by such explanation that the new compound when administered, takes in any way part in the activation or potentiation of the host defending mechanism of living mammals, resulting in the effective inhibition of the growth of bacteria and finally the disappearance of the bacteria. Thus, the compound MF-300 is a physiologically active compound with a low toxicity which can protect mammals from the infection by *Pseudomonas aeruginosa* E 2 and IFO-3455 and other bacterial strains, probably due to that the new compound even at an extremely low dosage brings some effect on the host defending mechanism of living mammals.

In view of the above, it is estimated that the compound MF-300 be useful as a medicine for prophylaxis and therapy of a variety of bacterial infections in men including infections caused by genus Pseudomonas.

According to a further aspect of this invention, therefore, there is provided a method of protecting mammals, including human beings, from bacterial infections which comprises administering a prophylactically or therapeutically effective amount of the compound MF-300 as hereinbefore defined to a mammal to be treated for prophylaxis or therapy of bacterial infections.

The compound MF-300 may be administered orally or parenterally, e.g. by intravenous and subcutaneous injections. The amount of the compound to be administered will, of course, vary depending upon the route and the number of times of administration, but usually the administration of 0.05~50 mg/kg may be suitable, e.g. for subcutaneous injection.

For the envisaged purposes, the compound MF-300 is usually administered in the form of a composition comprising the compound as active ingredient and a pharmaceutically acceptable carrier or adjuvant.

In a still further aspect, therefore, this invention provides a pharmaceutical composition for use to protect mammals against bacterial infections comprising as active ingredient an effective amount of the compound MF-300 as defined hereinbefore in combination with a pharmaceutically acceptable carrier or adjuvant. In a preferred embodiment, there is provided a water-soluble pharmaceutical composition for use to protect mammals against bacterial infections caused by *Pseudomonas aeruginosa*, comprising the compound MF-300 and a pharmaceutically acceptable, water-soluble carrier or adjuvant.

The composition according to this invention may contain varying amounts, and usually about 10~80% by weight, of the active ingredient.

The pharmaceutical composition may be formulated in the form of capsules, tablets, sugar-coated tablets, ampules, syrups, dispersions, suppositories and the like and may be prepared by any conventional formulation technique.

Figure 1:
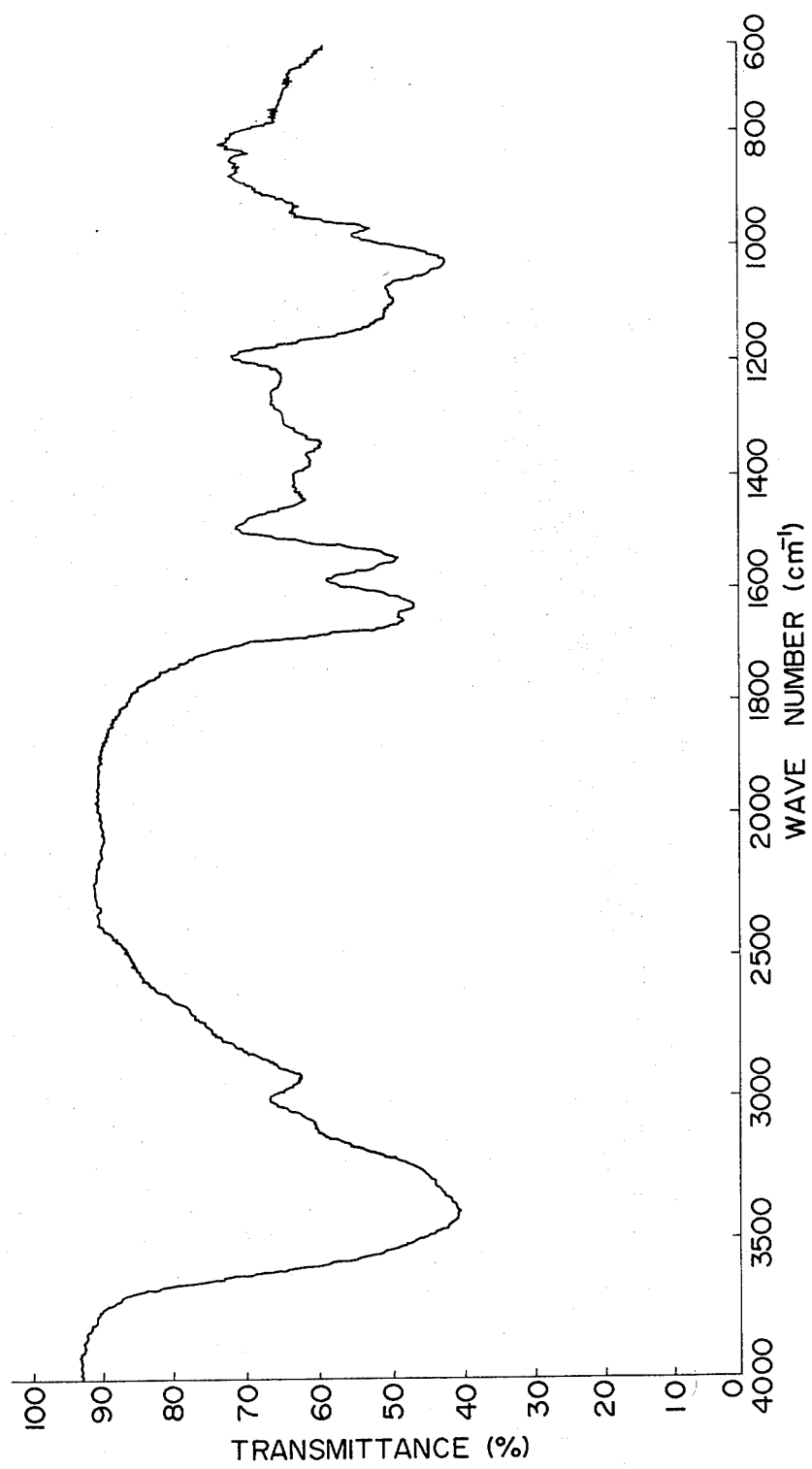
FIG. 1 shows a curve of the infrared absorption spectrum of MF-300.

The following Examples further illustrate the preparation of the compound MF-300.

EXAMPLE 1

Ribostamycin free base (20 g) is dissolved in a 50% aqueous dimethylformamide (132 ml) and triethylamine (13.2 ml) is added to the solution under stirring. Crotonoyl chloride (8.3 ml) is then added at a stroke to the solution and the mixture is stirred at room temperature overnight. The reaction mixture is then concentrated to dryness in vacuo, to which water (240 ml) is added to dissolve the residue. The solution is washed once with ethyl acetate (100 ml) and the aqueous layer isolated is concentrated to dryness in vacuo. The crude powder thus obtained is again dissolved in water (340 ml) and subjected to ultrafiltration using "Diaflow membrane PM 10". The residual fraction on the membrane is further subjected to ultrafiltration using "Diaflow membrane XM100A". The filtrate through the membrane XM100A is concentrated to dryness in vacuo to yield the desired compound MF-300 (122 mg).

Elemental analysis: C, 47.76; H, 7.21; N, 8.30; Cl, 5.02%.

Decomposition point: 195°~200° C.

Specific rotation: $[\alpha]_D^{25} + 38.2°$ (c 1.0, H₂O).

Infrared spectrum: as shown in FIG. 1.

Figure 2:
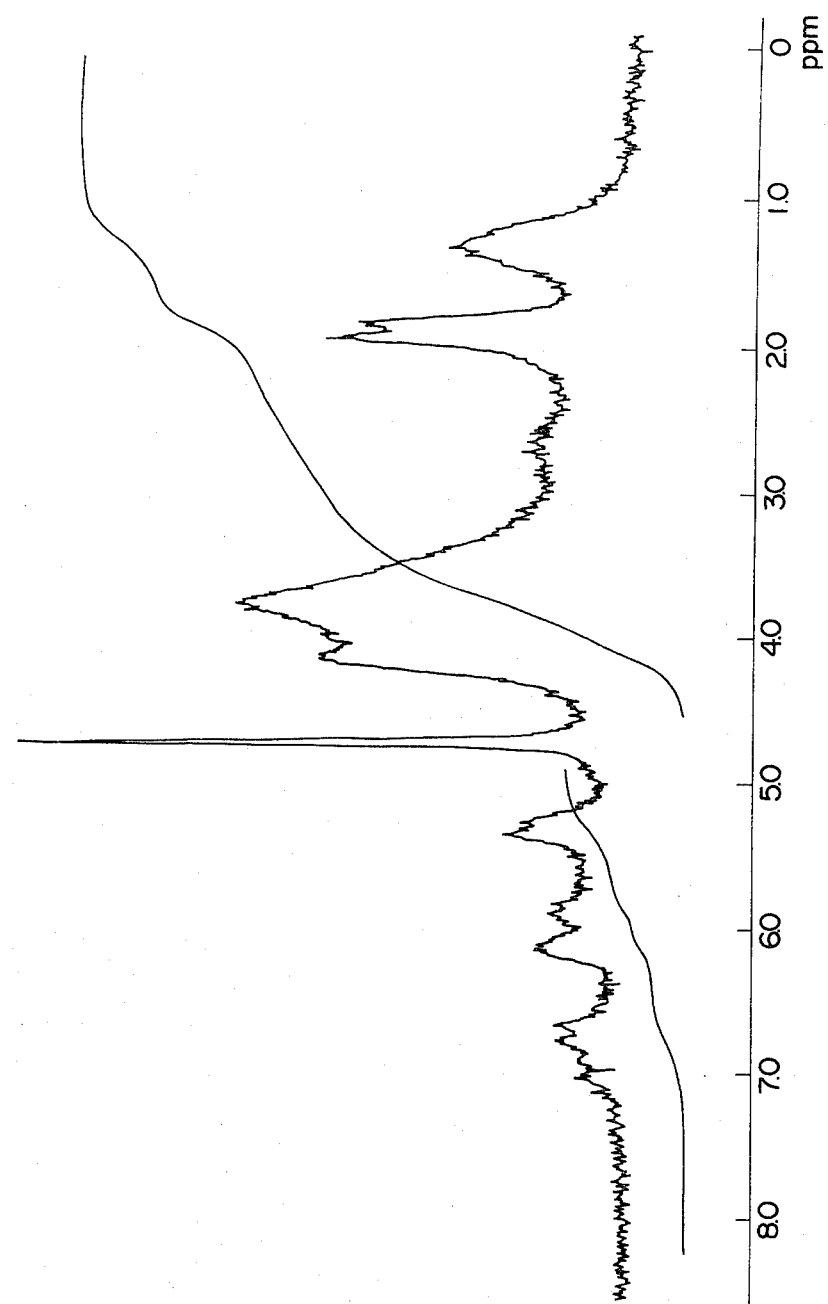
FIG. 2 shows a curve of the nuclear magnetic resonance spectrum of MF-300.

NMR spectrum: as shown in FIG. 2.

EXAMPLE 2

Ribostamycin free base (2 g) is dissolved in a 50% aqueous dimethylformamide (13.2 ml) and triethylamine (10.56 ml) is added to the solution under stirring. Then, crotonoyl chloride (6.64 ml) is added at a stroke to the solution and the resulting mixture is stirred at room temperature overnight. The reaction mixture is concentrated to dryness in vacuo, to which water (25 ml) is added to dissolve the residue. The solution is washed once with ethyl acetate (10 ml) and the aqueous layer isolated is concentrated to dryness in vacuo. The crude powder thus obtained is again dissolved in water (120 ml) and the solution is subjected to ultrafiltration using "Diaflow membrane PM 30". The residual fraction on the membrane is concentrated to dryness in vacuo to yield the desired compound MF-300 (182 mg).

Elemental analysis: C, 50.48; H, 7.15; N, 7.53; Cl, 5.35%.

Decomposition point: 195°~198° C.

Specific rotation: $[\alpha]_D^{25}+45.6°$ (c 1.0, H$_2$O).

The IR. and NMR. spectra of this product are same as those of the product of Example 1.

EXAMPLE 3

Ribostamycin free base (2 g) is dissolved in a 50% aqueous dioxane (13.2 ml) and triethylamine (1.32 ml) is added to the solution under stirring. Crotonoyl chloride (0.83 ml) is then added at a stroke to the solution and the mixture is stirred at room temperature overnight. The reaction mixture is concentrated to dryness in vacuo, to which water (25 ml) is added to dissolve the residue. The solution is washed once with ethyl acetate (10 ml) and the aqueous layer isolated is concentrated to dryness in vacuo. The crude powder thus obtained is again dissolved in water (30 ml) and the solution is ultrafiltered through "Diaflow membrane PM 30". The residual fraction on the membrane is concentrated to dryness in vacuo to yield the desired compound MF-300 (151 mg).

Elemental analysis: C, 47.32; H, 7.36; N, 8.28; Cl, 5.10%.

Decomposition point: 179°~180° C.

Specific rotation: $[\alpha]_D^{25}+37.5°$ (c 1.0, H$_2$O).

The IR. and NMR. spectra of this product are same as those of the product of Example 1.

EXAMPLE 4

Ribostamycin free base (4 g) is dissolved in a 50% aqueous acetone (26.4 ml) and triethylamine (2.64 ml) is added to the solution under stirring. Crotonoyl chloride (1.66 ml) is then added at a stroke to the solution and the mixture is stirred at room temperature overnight. The reaction mixture is concentrated to dryness in vacuo, to which water (50 ml) is added to dissolve the residue. The resulting solution is washed once with ethyl acetate (20 ml) and the aqueous layer isolated is concentrated to dryness in vacuo. The crude powder thus obtained is again dissolved in water (32 ml) and the solution is ultrafiltered through "Diaflow membrane PM 30". The residual fraction on the membrane is concentrated to dryness in vacuo to yield the desired compound MF-300 (29 mg).

EXAMPLE 5

Ribostamycin free base (2 g) is dissolved in a 50% aqueous dimethylformamide (13.2 ml) and sodium carbonate (513 mg) is added to the solution under stirring. Crotonoyl chloride (0.83 ml) is then added at a stroke to the solution and the mixture is stirred at room temperature overnight. The reaction mixture is concentrated to dryness in vacuo, to which water (25 ml) is added to dissolve the residue. The resulting solution is washed once with ethyl acetate (10 ml) and the aqueous layer isolated is concentrated to dryness in vacuo. The crude powder thus obtained is again dissolved in water (30 ml) and the solution is ultrafiltered through "Diaflow membrane PM 30". The residual fraction on the membrane is concentrated to dryness in vacuo to yield the desired compound MF-300 (12 mg).

What we claim is:

1. A polymeric compound, MF-300, which is obtained by reacting 1 to 36 moles crotonoyl chloride per mole of ribostamycin, concentrating the reaction product and recovering therefrom the compound as a fraction having a range of molecular weights of 10,000~100,000 when measured by ultrafiltration method and which has the following properties:
   (1) Elemental analysis: C, 48.52±2.16%; H, 7.24±0.24%; N, 8.04±1.02%; Cl, 5.05±0.3%;
   (2) Molecular weight: 10,000~100,000, when measured by ultrafiltration; 15,000~70,000, when measured by ultracentrifuge;
   (3) Appearance: Pale yellow, amorphous powder;
   (4) Decomposition point: 170°~200° C.
   (5) Specific rotation: $[\alpha]_D^{25}+40.4°±7.3°$ (c 1.0, H$_2$O);
   (6) Infrared absorption: 3400, 2940, 1660, 1630, 1550 cm$^{-1}$;
   (7) Ultraviolet absorption: No specific maximum absorption;
   (8) NMR spectrum: 1.0~1.5, 1.8~2.1, 3.2~4.2, 5.2~5.4, 5.6~6.3, 6.5~7.2 ppm;
   (9) Nature of aqueous solution: pH 4~6 (1% aqueous solution)
   (10) Solubility: Soluble in water and methanol; Insoluble in ethanol, chloroform, acetone and petroleum ether;
   (11) Color reaction: Positive to anthrone and Molisch reactions; Weakly positive to ninhydrin and biuret reactions; Negative to Tollens reaction.

2. A process for the preparation of the polymeric compound MF-300 defined in claim 1 which comprises reacting 1 to 36 moles crotonoyl chloride per mole of ribostamycin in an aqueous organic solvent in the presence of a base, concentrating the reaction product and recovering therefrom a fraction having a range of molecular weights of 10,000~100,000 when measured by ultrafiltration method.

3. A process according to claim 2 wherein the recovery of fraction is carried out by ultrafiltration.

4. A pharmaceutical composition for use to protect mammals against bacterial infections caused by bacteria of genus Pseudomonas, comprising as active ingredient an effective amount of the compound MF-300 defined in claim 1 in combination with a pharmaceutically acceptable carrier or adjuvant.

* * * * *